United States Patent [19]

Gaster

[11] 4,221,741
[45] Sep. 9, 1980

[54] PREPARATION OF 4(6'-METHOXY-2'-NAPHTHYL)BUTAN-2-ONE

[75] Inventor: Laramie M. Gaster, Sawbridgeworth, England

[73] Assignee: Beecham Group Limited, Great Britain

[21] Appl. No.: 4,888

[22] Filed: Jan. 19, 1979

[30] Foreign Application Priority Data

Jan. 27, 1978 [GB] United Kingdom ............... 03481/78

[51] Int. Cl.$^2$ ...................... C07C 45/00; C07C 49/84
[52] U.S. Cl. .................................. 568/314; 568/315; 568/318; 568/328
[58] Field of Search ............ 260/595, 590 FA, 590 R, 260/593 R

[56] References Cited

U.S. PATENT DOCUMENTS

| 3,880,932 | 4/1975 | Anderson et al. | 260/590 R |
| 3,994,869 | 11/1976 | Gontary et al. | 526/1 |

OTHER PUBLICATIONS

Sprague et al., J.A.C.S., vol. 57, pp. 2669–2675 (1934).
Gindin et al., Zhu, Org. Khim, vol. 9, #9, pp. 1985–1986 (1973).
House Acylation of active methylene compounds under basic conditions, pp. 749–751 (1967).
Patai, The Chemistry of the Carbonyl Compd, pp. 273–274 (1966).

*Primary Examiner*—Natalie Trousof
*Assistant Examiner*—James H. Reamer
*Attorney, Agent, or Firm*—Jacobs & Jacobs

[57] ABSTRACT

This invention provides a process for the preparation of 4-(6'-methoxy-2'naphthyl)-butan-2-one, which process comprises the hydrogenation of 4-(6' methoxy-2'-naphthyl)-4-hydroxy-but-3-en-2-one.

6 Claims, No Drawings

PREPARATION OF 4(6'-METHOXY-2'-NAPHTHYL)BUTAN-2-ONE

The present invention provides a novel chemical synthesis of 4-(6'methoxy-2'-naphthyl)butan-2-one and intermediates useful in that synthesis.

4-(6'-Methoxy-2'-naphthyl)butan-2-one is an anti-inflammatory agent first described and characterised in Belgian Patent No. 819794. A new synthesis of 4-(6'-methoxy-2'-naphthyl)-butan-2-one has been discovered which offers considerable advantages in ease of operation, yield and purity of product.

Accordingly, the present invention provides a process for the preparation of 4-(6'-methoxy-2'-naphthyl)-butan-2-one which comprises the catalytic hydrogenation of 4-(6'-methoxy-2'-naphthyl)-4-hydroxy-but-3-en-2-one.

Schematically this may be represented by:

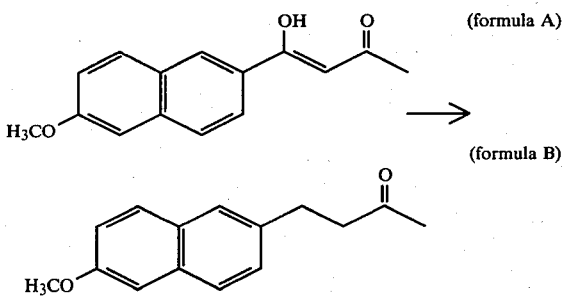

The hydrogenation may be effected using a low or medium pressure of hydrogen, for example 0.5 to 1.5 atmospheres of hydrogen. It is frequently convenient to carry out the hydrogenation reaction using an atmospheric or slightly super-atmospheric pressure of hydrogen. High pressures of hydrogen should be avoided as this can cause contamination of the end product with the corresponding substituted butanol.

The catalyst chosen for the reaction may be any conventional non-extreme transition metal catalyst but it has been found that palladium gives particularly acceptable results. A suitable catalyst is 10% palladium on carbon but higher or lower concentrations of the palladium on the support may be used and other conventional supports may replace the carbon if desired.

The reduction reaction is normally carried out at a non-extreme temperature such as $-20°$ C. to $+50°$ C., more usually from $0°$ C. to $30°$ C., for example, from $15°$ C. to $25°$ C.

The hydrogenation is normally brought about in an inert organic solvent such as ethanol, ethyl acetate, tetrahydrofuran, acetic acid or the like. When a neutral solvent is employed, the addition of an acid catalyst is advantageous.

In general the product obtained from this process is in the form of a white or off-white solid. Occasionally the product is obtained in the form of a yellowish material but conventional washing procedures can be used to convert this into a material of good pharmaceutical quality.

It will be appreciated that the novel 4-(6'-methoxy-2'-naphthyl)-4-hydroxy-but-3-en-2-one [which may also be named 4-(6'-methoxy-2'-naphthyl)butan-2,4-dione] forms an important aspect of this invention.

In order to facilitate the preparation of the 4-(6'-methoxy-2'-naphthyl)butan-2-one it is desirable that the 4-(6'-methoxy-2'-naphthyl)-4-hydroxy-but-3-en-2-one employed is as pure as possible; this invention accordingly provides a process for its purification which comprises contacting an impure solution of 4-(6'-methoxy-2'-naphthyl)-4-hydroxy-but-3-en-2-one with a solution of a cupric salt, obtaining the copper chelate therefrom, treating the chelate with an acid and thereafter isolating the released 4-(6'-methoxy-2'-naphthyl)-4-hydroxy-but-3-en-2-one.

Generally each step of this process is carried out at a roughly ambient temperature, for example from $12°$ C. to $30°$ C.

Normally the impure solution of the compound of formula A comprises an inert organic solvent such as methanol, chloroform, dichloromethane or the like. Normally the solution of the copper salt comprises an aqueous solution of cupric acetate, cupric chloride, cupric sulphate or the like.

The chelate once formed is obtainable by filtration.

In general the compound of the formula A is regenerated from the chelate by treatment with a strong inorganic acid such as hydrochloric acid.

The pure compound of the formula A is a favoured aspect of this invention.

This invention also provides a process for the preparation of 4-(6'-methoxy-2'-naphthyl)-4-hydroxy-but-3-en-2-one which comprises the base-catalysed reaction of 2-acetyl-6-methoxynaphthalene with a compound of formula $CH_3COX$, where X is a good leaving group. Esters of acetic acid are particularly suitable.

Particularly suitable esters of acetic acid for use are hydrocarbyl esters of up to 8 carbon atoms, especially lower alkyl esters such as the methyl, ethyl or like ester.

The condensation reaction is normally effected in an inert organic solvent such as dimethyl sulphoxide, dimethylformamide, dimethoxyethane or the like at a non-extreme temperature such as $0°$ C. to $100°$ C., for example $25°$ C. to $80°$ C.

The bases used to catalyse this reaction are preferably those of low nucleophilicity such as sodium hydride or its chemical equivalents.

From a further view point this invention provides a multistage process for the preparation of 4-(6'-methoxy-2'-naphthyl)butan-2-one which comprises reacting 2-acetyl-6-methoxynaphthalene with an acetic acid ester in the presence of a base to yield 4-(6'-methoxy-2'-naphthyl)-4-hydroxy-but-3-en-2-one and thereafter reducing the thus-formed 4-(6'-methoxy-2'-naphthyl)-4-hydroxy-but-3-en-2-one by catalytic hydrogenation to yield the desired 4(6'-methoxy-2'-naphthyl)butan-2-one.

It is frequently advantageous to include in this process the purification stage previously described.

The following Examples illustrate the invention:

EXAMPLE 1

Preparation of 4-(6'-methoxy-2'-naphthyl)-4-hydroxy-but-3-en-2-one

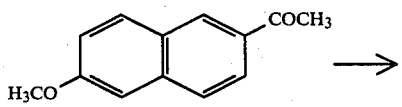

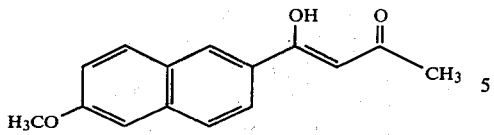

Ethyl acetate (0.04 mol) was added to a mixture of sodium hydride (0.04 mol) in dry dimethyl sulphoxide (20 ml) under nitrogen. 2-Acetyl-6-methoxynaphthalene (0.02 mol) in dry dimethyl sulphoxide (20 ml) was added over 40 minutes. During the addition the internal temperature rose to 50° C. The reaction mixture was maintained at 60° C. for 3½ hours, and then allowed to cool. 2.5 N HCl (100 ml) was carefully added and the product extracted into ether (3×50 ml). After washing with water (3×20 ml), drying (MgSO₄) and concentrating the solvent, a yellow solid was obtained which was recrystallised once from petroleum ether (100°–120°) to give 84% yield of 4-(6'-methoxy-2'-naphthyl)-4-hydroxy-but-3-en-2-one m.p. 116°–118° C.

EXAMPLE 2

Purification of 4-(6'-methoxy-2'-naphthyl)-4-hydroxy-but-3-en-2-one.

A solution of 20 g of the compound of Example 1 in chloroform (200 ml) was treated with 10% aqueous cupric acetate solution (200 ml). The mixture was stirred for ¾ hours and the precipitated copper chelate removed by filtration and washed with ether (2×100 ml) and water (2×100 ml). It was redissolved in chloroform (600 ml) and treated with 5 N HCl (300 ml). The mixture was stirred for about ¾ hour and the organic layer separated, washed with water (2×100 ml), dried (MgSO₄) and concentrated to give the title compound (18 g, 90%) m.p. 122.5°–125° C.

This compound exists as a mixture of diketone and ketoenol forms, in which the keto-enol form predominates.

'H NMR (CDCl₃)δ 7.05–8.3 (m, 6H), δ 6.24 (s, 1H). δ 3.89 (s, 3H), δ 2.17 (s, 3H).

Analysis req: C: 74.36; H: 5.82. Fnd: C: 74.03; H: 5.94.

EXAMPLE 3

Preparation of 4-(6'-methoxy-2'-naphthyl)butan-2-one

A solution of 4-(6'-methoxy-2'-naphthyl)-4-hydroxy-but-3-en-2-one (0.5 g, 0.00208 mole) in glacial acetic acid (50 ml) [effected by warming] was shaken in an atmosphere of hydrogen over 10% palladium on charcoal catalyst (0.05 g) at room temperature and atmospheric pressure until hydrogen uptake had ceased (approximately 2 hours).

The catalyst was then removed by filtration and the filtrate concentrated in vacuo. The remaining brown oil was dissolved in ether and this solution washed with sodium bicarbonate solution, then water and dried (MgSO₄). Evaporation of solvent gave a pale yellow oil (0.47 g, 93%) which solidified on standing at room temperature to an off-white solid.

What we claim is:

1. A process for the preparation of 4-(6'-methoxy-2'-naphthyl)-butan-2-one which comprises catalytic hydrogenation of 4-(6'-methoxy-2'-naphthyl)-4-hydroxy-but-en-2-one over a palladium catalyst at a hydrogen pressure of 0.5 to 1.5 atmospheres.

2. A process according to claim 1 wherein the catalyst is 10% palladium on carbon.

3. A process according to claim 1 wherein an acid catalyst is present.

4. A process according to claim 3 wherein the acid catalyst is acetic acid.

5. The compound 4-(6'-methoxy-2'-napthyl)-4-hydroxy-but-3-en-2-one and its tautomeric keto-enol equilibrium form, 4-(6'-methoxy-2'napthyl)-buta-2,4-dione.

6. A process for the preparation of 4-(6'-methoxy-2'-naphthyl)butan-2-one, which process comprises allowing 2-acetyl-6-methoxynaphthalene to react with an acetic acid ester in the presence of a base to yield the product 4-(6'-methoxy-2'-naphthyl)-4-hydroxy-but-3-en-2-one and thereafter catalytically hydrogenating said product over a palladium catalyst at a hydrogen pressure of 0.5 to 1.5 atmospheres.

* * * * *